(12) United States Patent
Penny et al.

(10) Patent No.: US 12,193,776 B2
(45) Date of Patent: *Jan. 14, 2025

(54) DYNAMIC SCALING FOR A ROBOTIC SURGICAL SYSTEM

(71) Applicant: Asensus Surgical US, Inc., Durham, NC (US)

(72) Inventors: Matthew Robert Penny, Holly Springs, NC (US); Alexander John Maret, Apex, NC (US); Kevin Andrew Hufford, Cary, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,348

(22) Filed: Oct. 31, 2022

(65) Prior Publication Data

US 2023/0050243 A1 Feb. 16, 2023

Related U.S. Application Data

(60) Continuation of application No. 17/566,634, filed on Dec. 30, 2021, which is a division of application No.
(Continued)

(51) Int. Cl.
| | |
|---|---|
| *A61B 34/37* | (2016.01) |
| *A61B 1/04* | (2006.01) |
| *A61B 34/00* | (2016.01) |
| *A61B 90/00* | (2016.01) |
| *A61B 1/313* | (2006.01) |

(Continued)

(52) U.S. Cl.
CPC ............ *A61B 34/37* (2016.02); *A61B 1/04* (2013.01); *A61B 34/74* (2016.02); *A61B 34/77* (2016.02); *A61B 90/361* (2016.02); *A61B 90/37* (2016.02); *A61B 1/3132* (2013.01); *A61B 2017/00216* (2013.01); *A61B 2034/2059* (2016.02); *A61B 2034/2065* (2016.02);
(Continued)

(58) Field of Classification Search
CPC .......... A61B 34/37; A61B 1/04; A61B 34/74; A61B 34/77; A61B 90/361; A61B 90/37; A61B 1/3132; A61B 2017/00216; A61B 2034/2059; A61B 2034/2065; A61B 2034/254; A61B 2034/258; A61B 2034/302; A61B 1/012; A61B 2017/00203; A61B 5/021; A61B 5/024; A61B 5/0533; A61B 5/0816; A61B 5/163; A61B 90/98; A61B 2090/061
See application file for complete search history.

(56) References Cited

U.S. PATENT DOCUMENTS 6,004,271 A * 12/1999 Moore ................ A61B 8/4209
600/463
6,530,913 B1 * 3/2003 Giba ................ A61M 25/0144
604/95.04

(Continued)

*Primary Examiner* — Sanjay Cattungal

(57) ABSTRACT

A robotic surgical system in which the system applies a scaling factor between user input from a user input device and corresponding movements of the robotic manipulator. Scaling factors may be applied or adjusted based on detected conditions such as the type of instrument being manipulated, detected distance between multiple instruments being manipulated, user biometric parameters.

11 Claims, 7 Drawing Sheets

Related U.S. Application Data

16/931,425, filed on Jul. 16, 2020, now Pat. No. 11,751,959.

(60) Provisional application No. 62/874,967, filed on Jul. 16, 2019, provisional application No. 62/874,974, filed on Jul. 16, 2019, provisional application No. 62/874,960, filed on Jul. 16, 2019, provisional application No. 62/874,969, filed on Jul. 16, 2019.

(51) Int. Cl.
*A61B 17/00* (2006.01)
*A61B 34/20* (2016.01)
*A61B 34/30* (2016.01)

(52) U.S. Cl.
CPC ... *A61B 2034/254* (2016.02); *A61B 2034/258* (2016.02); *A61B 2034/302* (2016.02)

(56) References Cited

U.S. PATENT DOCUMENTS

| | | | | |
|---|---|---|---|---|
| 6,544,230 B1* | 4/2003 | Flaherty | ............... | A61B 17/22 604/164.12 |
| 6,610,007 B2* | 8/2003 | Belson | ............... | A61B 1/008 604/95.01 |
| 6,669,709 B1* | 12/2003 | Cohn | ............... | A61B 17/11 606/167 |
| 6,905,460 B2* | 6/2005 | Wang | ............... | A61B 34/77 600/102 |
| 7,371,210 B2* | 5/2008 | Brock | ............... | A61B 34/30 606/139 |
| 10,434,332 B2* | 10/2019 | Vilsmeier | ............... | A61B 6/50 |
| 11,045,269 B2* | 6/2021 | Sachs | ............... | A61B 17/3417 |
| 2001/0009976 A1* | 7/2001 | Panescu | ............... | A61B 5/7435 600/424 |
| 2001/0029366 A1* | 10/2001 | Swanson | ............... | A61B 18/1492 606/29 |
| 2002/0087169 A1* | 7/2002 | Brock | ............... | A61B 17/0469 606/139 |
| 2002/0177789 A1* | 11/2002 | Ferry | ............... | A61B 34/73 600/585 |
| 2003/0074011 A1* | 4/2003 | Gilboa | ............... | A61B 5/06 606/130 |
| 2003/0135204 A1* | 7/2003 | Lee | ............... | B25J 9/104 606/1 |
| 2004/0176751 A1* | 9/2004 | Weitzner | ............... | A61B 34/32 606/1 |
| 2004/0193146 A1* | 9/2004 | Lee | ............... | A61B 17/062 606/1 |
| 2005/0182295 A1* | 8/2005 | Soper | ............... | A61B 1/2676 600/117 |
| 2007/0060879 A1* | 3/2007 | Weitzner | ............... | A61B 17/12136 604/95.04 |
| 2008/0300592 A1* | 12/2008 | Weitzner | ............... | A61M 25/0113 606/41 |
| 2009/0054884 A1* | 2/2009 | Farley | ............... | A61B 18/1492 606/41 |
| 2017/0071681 A1* | 3/2017 | Peine | ............... | A61B 34/74 |
| 2020/0179068 A1* | 6/2020 | Peine | ............... | A61B 34/37 |
| 2020/0367984 A1* | 11/2020 | Peine | ............... | B25J 9/1666 |
| 2021/0059781 A1* | 3/2021 | Peine | ............... | A61B 34/37 |
| 2021/0085304 A1* | 3/2021 | Penny | ............... | A61B 17/00234 |
| 2021/0298850 A1* | 9/2021 | Huang | ............... | A61B 34/35 |

\* cited by examiner

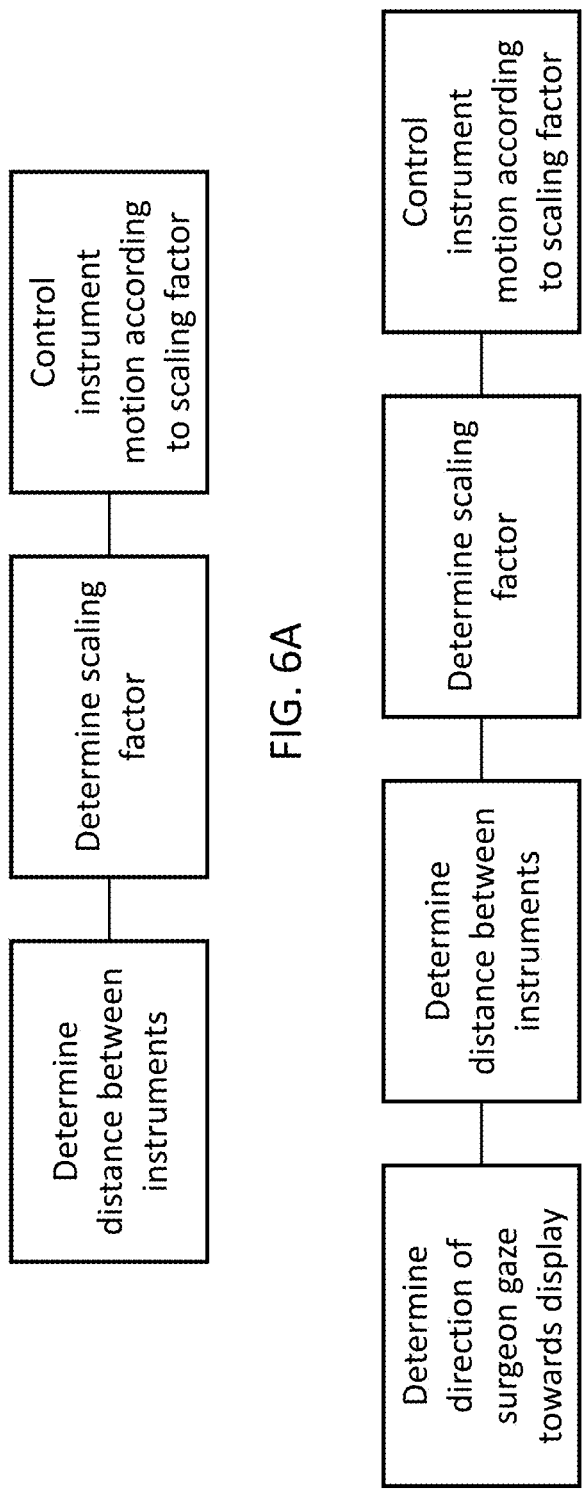
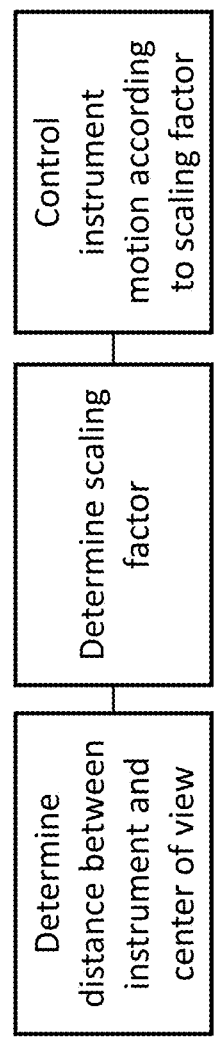
FIG. 6A
FIG. 6B
FIG. 6C

DYNAMIC SCALING FOR A ROBOTIC SURGICAL SYSTEM

This application is a continuation of U.S. application Ser. No. 16/931,425, filed Jul. 16, 2020, which claims the benefit of each of the following U.S. Provisional Applications: U.S. 62/874,960, filed Jul. 16, 2019, U.S. 62/874,967, filed Jul. 16, 2019, 62/874,969, filed Jul. 16, 2019 and 62/874,974, filed Jul. 16, 2019.

BACKGROUND

Surgical robotic systems are typically comprised of one or more robotic manipulators and a user interface. The robotic manipulators carry surgical instruments or devices used for the surgical procedure. A typical user interface includes input devices, or handles, manually moveable by the surgeon to control movement of the surgical instruments carried by the robotic manipulators. The surgeon uses the interface to provide inputs into the system and the system processes that information to develop output commands for the robotic manipulator. Some systems allow the user to optimize the ergonomics of the interface by "clutching," which means temporarily disabling output motion at the surgical instrument in response to movement of the input device, to allow the surgeon to move the input device to a position that allows the surgeon to more comfortably manipulate the handle.

Some systems may include predetermined or user-selectable motion scaling, in which a scaling factor is applied between the velocity of motion of the user input given at the input devices and the resulting velocity at which the corresponding robotic manipulator moves the surgical instrument. Surgeons may desire a fine scaling motion for certain procedures or steps, while in others s/he may prefer larger motion, relative to the movement of the user interface.

Motion scaling enables a surgeon to increase precision (fine robotic motions for large user input device motions) or increase range of motion and surgeon comfort (large robotic motions for small user input device motions). Motion scaling and the goal of surgeon comfort also give rise to the concept of clutching, wherein a surgeon repositions the grips/handles of the input devices while robotic motion is disengaged. Reducing the need for clutching may be desirable for some users since clutching can add time to the procedure.

Highly scaled-down motion (i.e. fine robotic motion for large input device motions) requires frequent clutching and increases the surgeon's effort, due to the fact that the surgeon moves the user input devices essentially twice as often as the robot moves the instrument.

In some surgical systems, the user has the ability to select different levels of motion scaling to adjust the mapping of the magnitude of motion at the input device to the magnitude of motion at the output device. This functionality can be useful to enable the user to adjust the sensitivity of the system to motion to better suit different surgical situations depending on the level of precision required. With these systems, users select the motion scaling setting from a menu, which requires them to stop performing surgical tasks to make a change. This results in a delay in the procedure as the user switches scaling settings between a high precision task in a small workspace in the body cavity and another task requiring larger motions. The concepts described in this application improve the efficiency of the surgical procedure by enabling dynamic scaling in which the motion scaling settings are adjusted during use either autonomously or by the user without requiring the procedure to pause. Ideally, this solution will allow the manipulator to move as the user wants and expects over a wide variety of tasks without any need for the user to think about or potentially even notice changes in the motion scaling.

This application describes a system and method configured to tune the motion scaling applied between the input given at the user input device and the resulting motion of the surgical instrument by the robotic manipulator. In some embodiments, the system automatically tunes the motion scaling as appropriate for the current surgical context. In some embodiments, the system predicts the desired motion scaling factor based on the instrument that is or has been mounted to a robotic manipulator, and/or based on the task or tasks the system determines are being carried out or are expected to be carried out by the user. In other embodiments, the system automatically varies a scaling factor during the course of a surgical procedure based on input to the system regarding the procedure or steps being performed.

BRIEF DESCRIPTION OF THE DRAWINGS

FIGS. 6A-6C show functional block diagrams illustrating methods of determining a scaling factor based on instrument distance.

DETAILED DESCRIPTION

Figure 1:
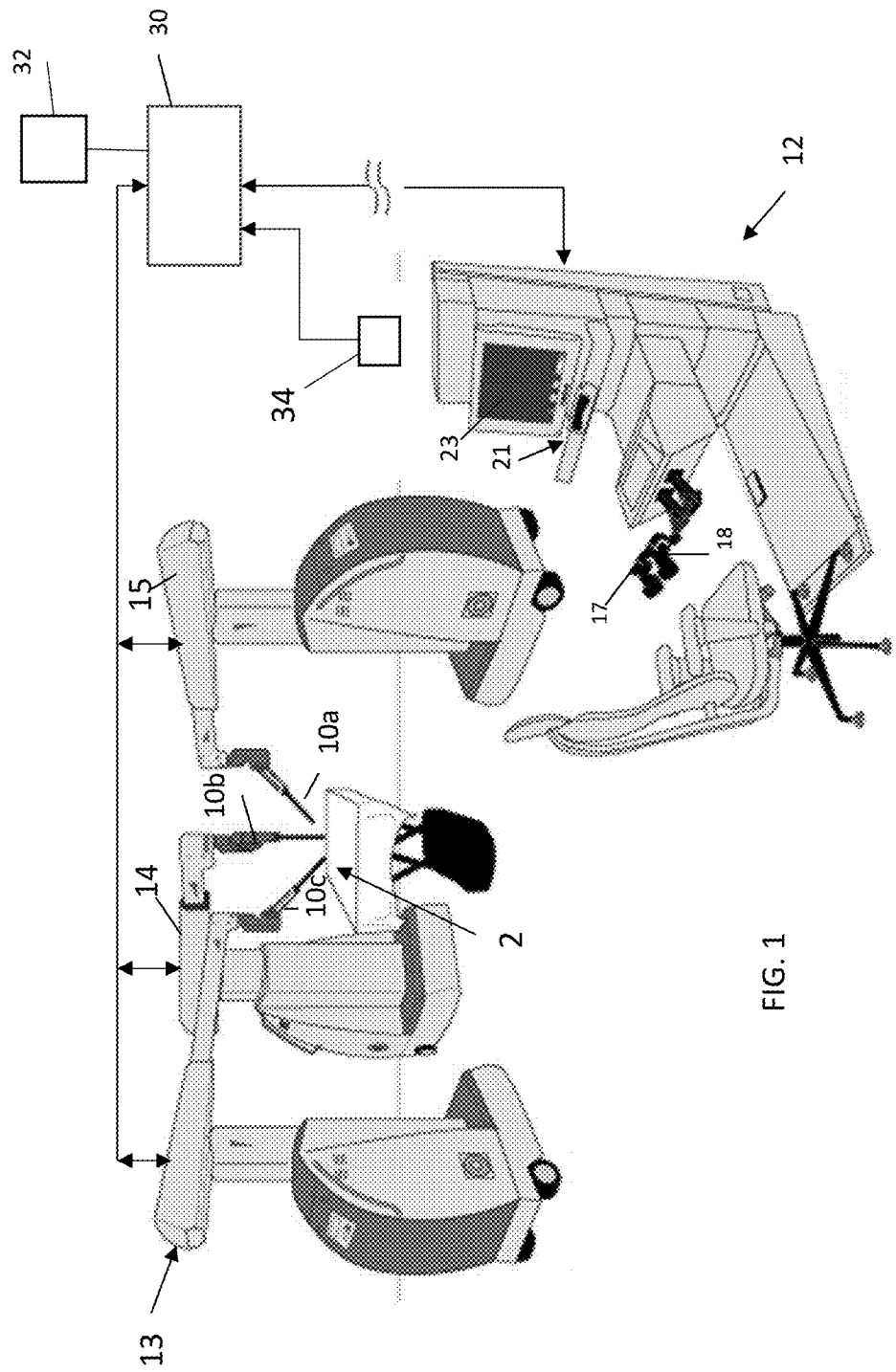
FIG. 1 shows an example of a robot-assisted surgical system.

Although the inventions described herein may be used on a variety of robotic surgical systems, the embodiments will be described with reference to a system of the type shown in FIG. 1. In the illustrated system, a surgeon console 12 has two input devices such as handles 17, 18. The input devices 12 are configured to be manipulated by a user to generate signals that are used to command motion of a robotically controlled device in multiple degrees of freedom. In use, the user selectively assigns the two handles 17, 18 to two of the robotic manipulators 13, 14, 15, allowing surgeon control of two of the surgical instruments 10*a*, 10*b*, and 10*c* disposed at the working site at any given time. To control a third one of the instruments disposed at the working site, one of the two handles 17, 18 is operatively disengaged from one of the initial two instruments and then operatively paired with the third instrument. A fourth robotic manipulator, not shown in FIG. 1, may be optionally provided to support and maneuver an additional instrument.

One of the instruments 10a, 10b, 10c is a camera that captures images of the operative field in the body cavity. The camera may be moved by its corresponding robotic manipulator using input from a variety of types of input devices, including, without limitation, one of the handles 17, 18, additional controls on the console, a foot pedal, an eye tracker 21, voice controller, etc. The console may also include a display or monitor 23 configured to display the images captured by the camera, and for optionally displaying system information, patient information, etc.

The input devices 17, 18 are configured to be manipulated by a user to generate signals that are processed by the system to generate instructions used to command motion of the manipulators in order to move the instruments in multiple degrees of freedom. A control unit 30 is operationally connected to the robotic arms and to the user interface. The control unit receives the user input from the input devices corresponding to the desired movement of the surgical instruments, and generates commands to cause the robotic manipulators to maneuver the surgical instruments accordingly.

Where the system includes an eye tracker, input from the eye tracker 21 may be used to determine the direction of the user's gaze towards the displayed image, and signals are generated to move the manipulator holding the camera to move the camera towards the site within the patient corresponding to the region of the user's focus. Input from the eye tracker may also be used to determine an increase or decrease in the distance between the user's eyes and the display, and signals are generated to move the manipulator holding the camera away from or closer to, respectively, the site being observed by the camera. See commonly owned U.S. Pat. No. 9,360,934, which is incorporated herein by reference. Naturally, similar eye tracking input may be used to pan or zoom the image without moving the manipulator supporting the camera, such as by articulating the camera itself, performing digital pan/zoom etc.

One or more of the degrees of freedom of the input devices are coupled with an electromechanical system capable of providing gravity compensation for the user input, and/or providing haptic feedback to the surgeon. It should be understood that the concepts described in this application are not limited to any particular user input device configuration. Alternative configurations include, without limitation, those described in co-pending application Ser. No. 16/513,670 entitled HAPTIC USER INTERFACE FOR ROBOTICALLY CONTROLLED SURGICAL INSTRUMENTS, and user interfaces or haptic devices known to those of skill in the art or developed in the future.

The surgical system allows the operating room staff to remove and replace surgical instruments carried by the robotic manipulator, based on the surgical need. Once instruments have been installed on the manipulators, the surgeon moves the input devices to provide inputs into the system, and the system processes that information to develop output commands for the robotic manipulator in order to move the instruments and, as appropriate, operate the instrument end effectors. The user interface may be one that allows the surgeon to select motion scaling factors as well as to clutch and reposition the handles to a more comfortable position. In some cases, the surgeon may desire a fine scaling motion, while in others s/he may prefer larger motion, relative to the movement of the user interface. These desires may be situation-dependent and may be predictable based on the procedure and the sequence of installed instruments.

Instrument Type Based or Context-Based Motion Scaling

In a first embodiment, the system is configured to identify the type of surgical instrument that is attached to, or approaching for attachment to, one of the system's manipulators. For this purpose, the system preferably includes a sensor 32. The sensor is positioned to determine the type of instrument that a user is in the process of engaging with a manipulator, or that the user has engaged with the manipulator. The location of the sensor depends on the type of sensor used. It may be on the manipulator, in proximity to the manipulator within range to sense or read or information carried by or on the surgical instrument or to sense, detect, or read a property of the surgical instrument. Without limiting the scope of the claims, the following are non-limiting examples of sensors that may be used for this purpose. Each of these may be positioned on the relevant robotic manipulator, or in proximity to the manipulator:

(i) an RFID reader/antenna or near field communication sensor, that reads information relating to the type, serial number, geometry, or other identity-related information, that is electronically stored on a portion of the instrument or a component attached to the instrument. In the RFID context the device storing the information is sometimes referred to as an "RFID tag."

(ii) a circuit that reads such information from a memory device that is carried by the instrument when the instrument is placed in electronic communication with the circuit upon its mounting to the manipulator;

(iii) an optical sensor, optical scanner, or image sensor. Such a sensor may generate an output based on a property of the instrument or a device attached to the instrument (e.g. a code, symbol, marker, text, color of or on the surgical instrument) using, in some cases, computer vision or image processing techniques. In some embodiments, a laparoscopic camera positioned within the patient's body cavity, and optionally supported by a robotic manipulator, may be used to capture images of the portion of the instrument disposed within the body, and computer vision or image processing techniques then used to determine a code, symbol, marker, text, colors, shapes etc. of or on the surgical instrument;

(iv) a sensor that detects when mechanical components on the manipulator arm are moved by the mounting of instruments, for example in a configuration where each different type of instrument produces a different amount or type of movement of the mechanical components when mounted. See for example concepts for giving mechanical input of the type described in U.S. application Ser. No. 15/975,965, Instrument End Effector Identification, which is incorporated herein by reference.

The system is optionally configured to further receive input or information that identifies, or from which the processor can identify, the surgical procedure that is to be performed. Any type of communication device used to electronically give input to the system can be used to identify the type of procedure to the system. This might include a graphical user interface together with an input device such as a touch screen, head tracker, mouse, eye tracker 21 (e.g. allowing the user to look at an icon, image, words, etc. and confirm a selection using another input device such as a foot pedal or switch at the surgeon console).

The system includes at least one processor (which may be part of control unit 30) and at least one memory. The memory stores instructions executable by the one processor to perform the various functions described herein. The memory also includes a database storing scaling factors. Within the database, are predetermined scaling factors for various instrument types. For example, a particular scaling factor might be correlated with a first instrument type (e.g. a Maryland dissector) and a second, different, scaling factor might be correlated with a second instrument type (e.g. a needle holder). If it is beneficial for a given instrument type to operate using a different scaling factor for different procedures, the scaling factor data may be further correlated by procedure type. Scaling factors might be further correlated based on any combination of the following factors: procedure type (i.e. the type of surgery being performed), task type (i.e. the type of surgical steps that instrument can be used for), particular users (in other words, each user's preferred scaling factor for that instrument type, and/or for that instrument type for a particular procedure, and/or for that instrument type for a particular surgical task), etc. The database might further include data correlating surgical procedures to typical sequences of instrument exchanges and/or tasks that typically occur during that procedure. This may be further correlated to both procedure type and user, since different users may use different sequences of instrument exchanges for the same procedure.

The database further includes data correlating input of the type that may be received from the sensor 32 with the various types of instruments available to be mounted to the robotic manipulator, allowing the system to determine based on the input what type of instrument has been, or is in the process of being, mounted to the manipulator.

Figure 2:
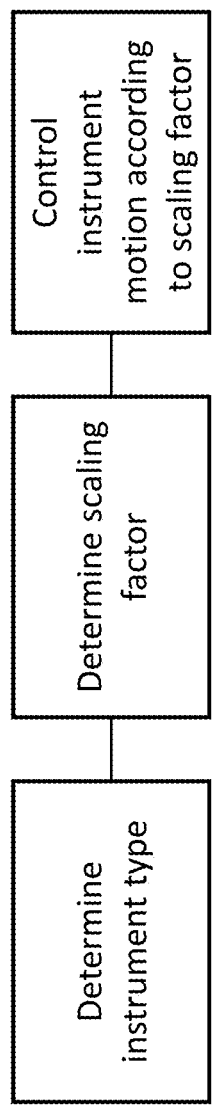
FIG. 2 shows a functional block diagram illustrating a first method of determining a scaling factor based on instrument type.

In one embodiment depicted in FIG. 2, the appropriate scaling factor is determined based solely on the instrument type as determined based on the sensor input. The system receives input from the sensor 32 as the instrument is moved in proximity to, or is mounted to, the corresponding robotic manipulator. Based on the input, the system determines the type of instrument, and determines from the database the type of scaling factor to be used for that type of instrument. The determined scaling factor is applied between the user input given at the relevant input devices (e.g. input device 17 or 18) and the resulting movement of the instrument by the robotic manipulator.

In a slightly modified version of the FIG. 2 embodiment, the system further receives user identification input. This may be done using any conventional form of input, such as touch screen, keyboard, mouse, scan of a user's identification wristband/badge, etc., any of the forms of input devices mentioned above. In some embodiments, the console may include sensor that allow the system to recognize the user based on biometric parameters sensed using sensors at the console (e.g. image sensors for facial recognition, eye scanners, fingerprint scanners, voice sensors). In this embodiment, scaling factors associated with that user and the relevant instrument type are retrieved from the database and used to control instrument motion.

Figure 3:
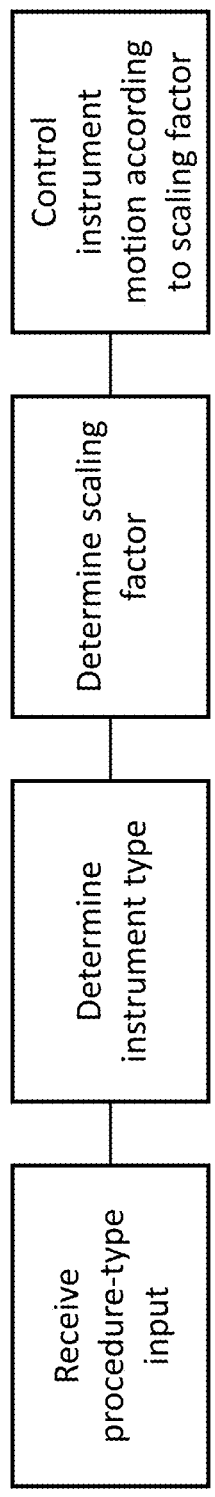
FIG. 3 shows a functional block diagram illustrating a second method of determining a scaling factor based on instrument type.

The embodiment depicted in FIG. 3 is similar to that shown in FIG. 2, but additionally includes a step in which the system receives procedure-type input, which may be input to the system using any suitable type of input device. Use of the robotic system incorporating this feature might include an initialization step in which the user identifies the intended surgical procedure to the system or selects the surgical procedure from options displayed at the console. In other embodiments, the system may determine the procedure type. For example, the database may include data correlating procedure types with certain aspects of the surgical set-up, such as which types of instruments are on each of the arms, the arrangement of the robotic manipulators relative to the patient bed (e.g. as determined by applying computer vision to images of the robotic manipulators and the patient bed, or the arrangement of instruments or trocars within the patient (e.g. as determined by applying computer vision to images of the patient once the trocars have been positioned or the instruments inserted through the trocars). Scaling factors associated with that procedure type and the relevant instrument type are thus retrieved from the database. As with the FIG. 2 embodiment, the system may further receive user identification input, and scaling factors associated with that user, the identified procedure type and the relevant instrument type are retrieved from the database and used to control instrument motion.

Figure 4:
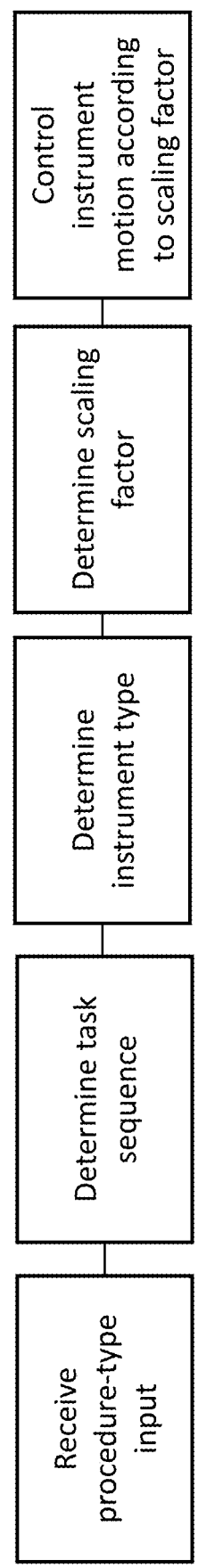
FIG. 4 shows a functional block diagram illustrating a third method of determining a scaling factor based on instrument type.

FIG. 4 illustrates an embodiment similar to FIG. 3, but in which, based on the identified surgical procedure and user, the processor determines using the database the typical sequence of instrument exchanges for that procedure or procedure and user, excluding any deviations or exceptions. For example, a cholecystectomy would typically begin with a grasper for retracting the fundus of the gallbladder, a second grasper and a Maryland grasper for assisting in the dissection of the triangle of calot. During the course of the procedure, as the processor receives input from the sensor in response to movement of an instrument into proximity or engagement to the manipulator, the processor obtains the scaling factor for that instrument (and, if applicable, that instrument and procedure) then adjusts the motion scaling of the system to an optimal ratio for the task at hand. This ratio could also factor in stored surgeon/user preferences, which would also be stored in the database.

The process is repeated each time an instrument exchange occurs. Thus, in the current example, after the Maryland grasper has been removed and a clip applier inserted, the system may adapt the motion scaling again, to an optimal ratio for the next task it anticipates that the user will perform. As the procedure continues and instruments are exchanged for one another, the system constantly updates the motion scaling factor according to what perceived step the surgeon is performing in the named procedure. If an instrument exchange is performed that produces an atypical combination or sequence of instruments for that procedure (i.e. the detected instrument is one not expected based on the procedure), the system may default to a standard motion scaling factor. The system may be further equipped to allow the user to override the dynamic scaling function or the scaling factor applied for a given step using input devices (e.g. the GUI, a dial on the input device 17, 18) at the surgeon console.

In a slightly modified embodiment, the concepts described above might be enhanced by task recognition performed using input from the camera 10b positioned in the body cavity. Thus, for example, if the system recognizes one, or a sequence of, tasks being performed that differs from the expected sequence, the processor might determine the procedure being performed based on the task or sequence of tasks, using data stored in the database correlating, for example, patterns or sequences of instrument movements or actuations with tasks. The processor may then cause the user to be advised of the determined procedure and prompted to confirm using an input device and/or the GUI that the determined procedure is being performed. If confirmed, the processor applies the scaling factors for the newly determined procedure, based on the information stored in the database.

While this discussion focuses on motion scaling, motion scaling is but one system feature that could be adjusted based on procedure type and instrument recognition. In another embodiment, the processor could be configured to adjust the functions controlled by various input devices (e.g. foot pedals, buttons, knobs or switches on the surgeon console or input handles) based on the installed instrument. For example, if a monopolar instrument is installed, a pair of foot pedals may be enabled with coagulation and cut functions attached, respectively. However, if the monopolar instrument is replaced with a suction irrigation device, the foot pedals may switch functionalities to flush and vacuum, respectively. As another example, upon determining that a stapler is being or has been mounted to a manipulator, the foot pedal may enable driving of the sled in the stapler end effector. The basis for this embodiment is to use the procedure type and installed instrument to automatically adjust the system for optimal performance, including, but not limited to, the aforementioned features of motion scaling and button/input device task assignment.

Figure 5:
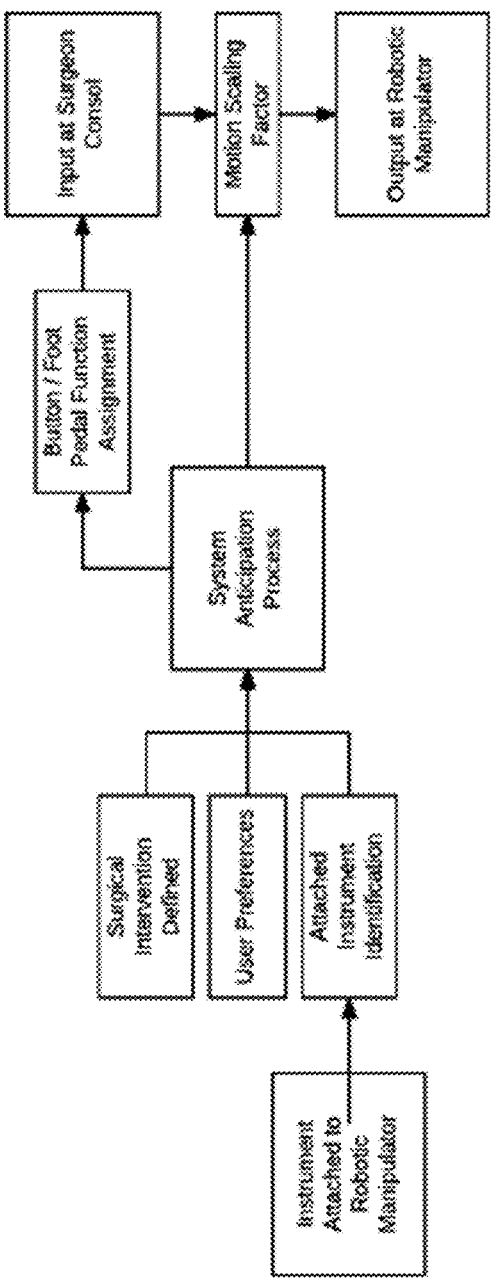
FIG. 5 is a process flow diagram illustrating flow for the third exemplary embodiment.

The system and method of the FIG. 4 embodiment offer the advantages of anticipating the next operative step in a procedure, based on the exchange of instruments and concurrent assignment to each arm, and the automatic adjustment of system features including motion scaling and button/input device function assignments according to the instruments attached to each robotic manipulator, or as they are assigned to each handle on the user interface. The FIG. 5 flow diagram illustrates the process flow for this type of system adjustment, based on procedure type and the instruments installed on the robotic manipulator. Note that a system may be configured to perform just one of the described functions (adjustment of scaling factors; adjustment of input device functionality etc.), or multiple ones based on the procedure type, instrument type, and (optionally) user identity or preference.

Scaling Based on Surgical Instrument Distance Data

In other embodiments, scaling factors may be dynamically adjusted based on information determined by the system relating to the operative site in the patient anatomy.

In these embodiments, the system includes features that allow the system to determine the distance between instrument end effectors disposed in the operative field, and that then adjust the amount of motion scaling based on that distance.

In these embodiments, the system includes a source of input to the system from which a determination of the distance between the end effectors of the surgical instruments can be made. The source may include input from sensors monitoring joint positions of the robotic manipulator so as to allow the position of a portion of the end effector (e.g. its tip) to be determined using kinematics. Alternatively, or in addition, the source may include input from a visual recognition system that recognizes the end effectors in the captured image data, allowing the distance between the end effectors to be calculated. For example, the camera 10b carried by the robotic manipulator may capture images of the distal ends of instruments 10a and 10c. As yet another example suitable for certain surgical systems, the input may instead or additionally come from sensors measuring joint positions at the user interface, and it is then used to determine the end effector position based on the end effector position that has been commanded using the user input device.

The system includes a processor coupled to a memory. The memory stores instructions executable by the processor to receive the input, determine the distance between the end effectors, apply a scaling factor based on the determined distance, and command motion of the robotic manipulator based on input from the user input device, as scaled using the applied scaling factor.

Figure 7:
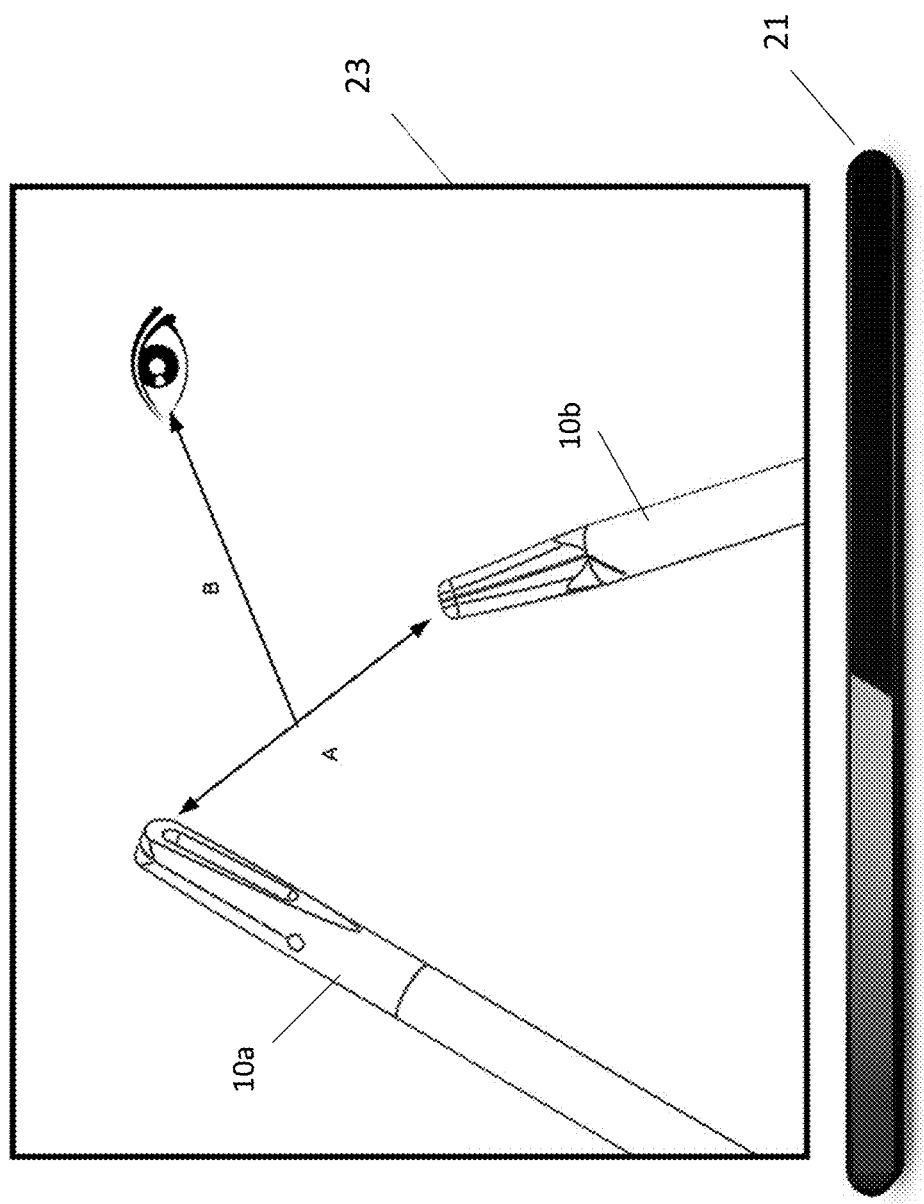
FIG. 7 shows a display displaying an intraoperative image of the surgical work site captured by the camera, and an eye tracking unit beneath the display, and further illustrates use of the system according to the FIGS. 6A and 6B embodiments.

For example, referring to FIG. 6A and FIG. 7, in one embodiment the system uses the image data or kinematic data to determine the distance between two or more instruments 10a, 10b (Vector A). A memory associated with the processor includes a database that stores scaling factors based on instrument distances. After determining the distance, the system obtains the relevant scaling factor, and adjusts or maintains the motion scaling based on this distance. Note that this scaling factor may be applied to either or both of the surgical instruments. In one application, when the surgeon is working in tighter spaces and the instrument tips are determined to be at or below a predetermined separation distance D, the system would reduce the motion scaling (e.g. movement of the relevant user interface 17 or 18 in a degree of freedom by a distance X would produce a corresponding motion at the end effector, in that degree of freedom, that is smaller than X), helping the surgeon to work with enhanced precision. Conversely, when the surgeon is working with instruments determined to be separated by a distance greater than D, the motion scaling would enable larger scale motions.

While in the above example, the system operates using two scaling factors (one of which may be 1), the instructions stored in memory for each of the described embodiments may include a plurality of scaling factors, each to be applied when the separation between the end effectors is within a different, predetermined, range. For example, the instructions might cause a first scaling factor to be applied when the end effectors are separated by a first distance range, a second scaling factor applied when the end effectors are separated by a second distance range, and a third scaling factor applied when the end effectors are separated by a third distance range.

In other embodiments, the processor calculates the scaling factor as a function of the determined distance, such that the scaling factor dynamically changes as the instruments are moved towards or away from one another.

The instructions optionally would be programmed to cause the processor to use a filter on the distance between instrument tips (i.e. moving average) to ensure that changes in motion scaling are smooth and fluid, and to avoid multiple scaling factor changes in short succession. Feedback to the user may be optionally given to notify the user of a change in the scaling factor. For example, a textual or graphical indication may be displayed on the image display, an auditory alert may be sounded, or a tactical alert may be generated, such as a vibration of the user input handle or another feature that is in contact with the user (e.g. the seat at the surgeon console). The alert might optionally prompt the user to give input to the system affirming that the surgeon would like the change in scaling factor to be applied. The affirmatory input may be given from any type of device that could deliver an input to the system. Non-limiting examples include an input control on the handle or elsewhere on the console or robotic system (as non-limiting examples, a switch, button, knob, key, lever, or touch input), a voice input device configured to receive verbal input, an eye tracker, head tracker, foot pedal etc.

The embodiment depicted in FIG. 6B and FIG. 7 performs a dynamic scaling function similar to the first embodiment, but changes in scaling are based on the distance between the location the surgeon is viewing on the image display and the instrument location as displayed on the display image, with the understanding that a close distance would indicate work that would benefit from fine scaling and a larger distance would not necessitate as a high a level of precision. In this embodiment the robot-assisted surgical system is equipped with a system capable of measuring the direction of the gaze of the surgeon towards the display at the surgeon console (e.g. eye tracker 21 in FIGS. 1 and 2) as well as a visual recognition system configured to identify the instrument end effectors in the intraoperative view. The processor operates according to a set of instructions in the memory to receive input from the visual recognition system and from the eye tracker, and to monitor the distance between the surgeon's gaze and the displayed instrument tip or end effector. For scenarios with more than one instrument, the system may either use the closest instrument tip to the surgeon's gaze or determine the centroid of the instruments within the view and monitor the distance between the centroid and the surgeon's gaze (Vector B in FIG. 6C). As with the FIG. 6A embodiment, based on this dimension monitored by the processor, dynamic adjustments would be made to dynamically adjust the motion scaling factor for the system. Also, as with the FIG. 6A embodiment, motion scaling may include a filter on the monitored dimension to ensure smooth transitions from different motion scaling factors.

Figure 8:
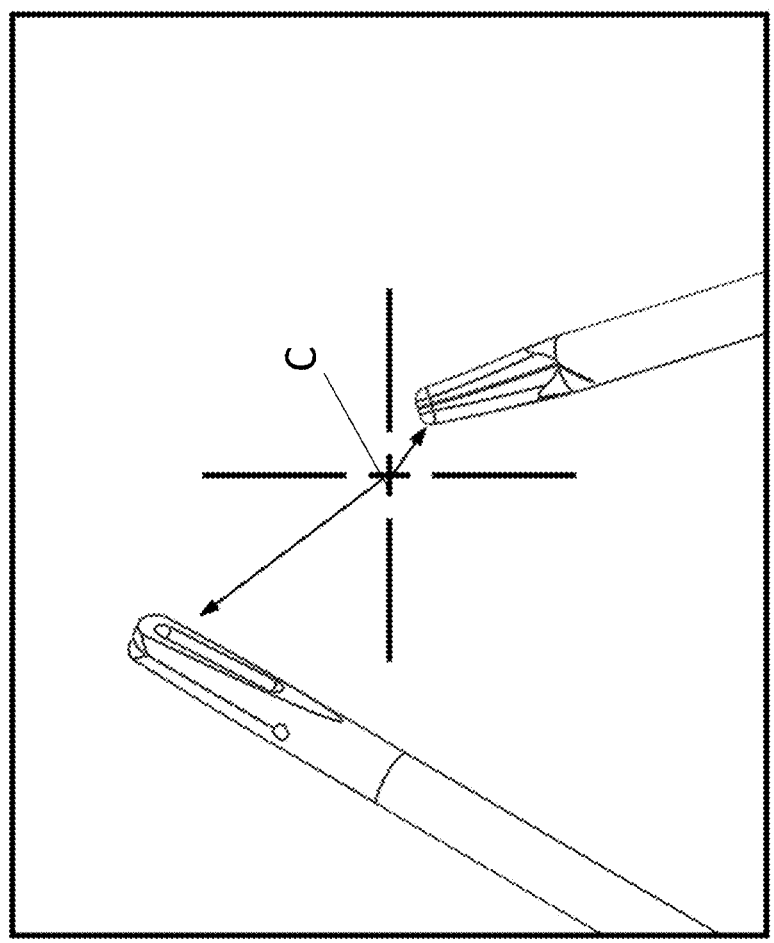
FIG. 8 shows a display displaying an intraoperative image of the surgical work site captured by the camera, and further illustrates use of the system according to the FIG. 6C embodiment.

The embodiment illustrated in FIG. 8 is similar to those described with respect to FIG. 7, and includes components allowing for identification of instrument end effectors displayed in the intraoperative view. Referring to FIG. 8, input relating to the end effector positions in the intraoperative view is used by the system to determine the distance between each instrument and the center C of the intraoperative view, as displayed on the monitor. The motion scaling factor is selected or adjusted based on the relative distance between the instrument tip and the center of the intraoperative. As with the first and second embodiments, the third embodiment would preferably use filtration to facilitate smooth transitions between scaling factors.

Figure 9:
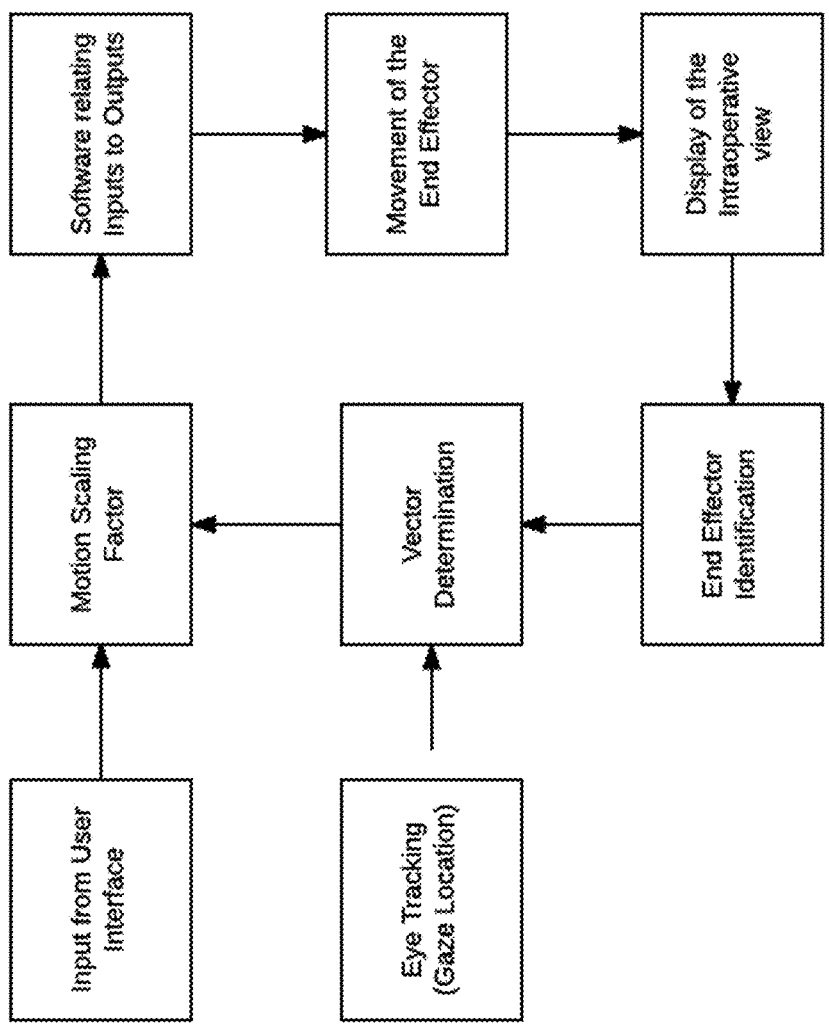
FIG. 9 schematically illustrates process flow for the FIG. 6A-6C.

The process flow chart of FIG. 9 illustrates aspects of the first, second and third embodiments.

User inputs to the system for causing movement of surgical instruments on the robotic manipulators are captured by the user interface. The motion scaling factor is used to relate the motion of the inputs to the motion of the outputs. Note that the motion scaling factor is broken out as a separate entity from the other aspects of the software for relating the user inputs to command outputs for the robotic manipulators, in order to make the flow chart clearer. The surgical instrument end effector is moved by the robotic manipulator.

The camera captures images of the end effector in the operative field and those images are displayed to the user on the display. The system then identifies the end effector location(s) using techniques described above, receives any other inputs required in defining the vector(s) (i.e. gaze location via eye tracker), and defines the relevant vector(s) as described above. The system then applies the applicable scaling factor based on the defined vector(s).

It should be noted that the distance-based scaling determinations may be further combined with concepts described above in connection with the instrument-based scaling. In other words, the database may correlate scaling factors with other data in addition to distance. Such other data may include any combination of: the type or types of instruments whose distance is being determined, procedure type, task type, and user.

The described system and method offer a number of advantages over existing technology, including adjustment of the motion scaling factor to meet the needs of the surgeon at a given moment in the procedure. Additionally, increasing scaling at points in the procedure eliminates or reduces the frequency of clutching for surgeon comfort by requiring less motion at the user input device to produce the desired motion of the surgical instrument.

Scaling Based on Surgeon Monitoring

In other embodiments, the system includes a sensor 34 configured to sense changes in a transient user parameter indicative of a change in the user's focus or emotional arousal. In other words, the sensor might be one that senses parameters representing physiological or behavioral characteristics. For this purpose, the system includes a sensor 34 positioned to monitor the user parameter. When the user is performing a critical task requiring high focus and small precise instrument movements, he/she may want the motion scaling to be set very low. However, at times the user will need to move an instrument a greater distance to reposition adjacent tissue or deal with a new and more urgent situation. At these moments, the user may prefer a higher motion scaling factor to enable larger instrument motions without repeated clutching of the input device.

In the disclosed system, the control system is configured to dynamically change the motion scaling factor based on data from the sensors which monitor the surgeon. The following concepts could be used to characterize the state of the surgeon and may offer opportunities for enhancing the user experience via dynamic motion scaling. These could be alone or in various combinations to create a maximally effective dynamic scaling control system.

1. User Blink Frequency

Decreased blink frequency may indicate an increased level of user focus. This heightened focus may be due to a critical moment in the procedure or reduced surgeon confidence. In this embodiment, the sensor is an image sensor positioned to capture images of at least one of the user's eyes. As one example, an eye tracker may be used. An image processing algorithm is used to identify when an eye is open or closed, allowing a determination of the user's blink rate. The blink rate is monitored during the procedure, and, in response to a detected decrease in blink rate frequency, the processor causes the motion scaling factor to be reduced to help the user move more carefully, deliberately, and precisely. Where the system includes an eye tracker 21 to give input that results in camera control or movement, or for some other purpose, that eye tracker may be used as the sensor 34 to generate input from which the processor can determine blink rate.

2. Change in Heart Rate or Blood Pressure

Changes in user vital signs such as heart rate or blood pressure can correlate to the level of user focus and/or stress. In this embodiment, the sensor 34 is a heart rate sensor (e.g. body worn electrodes or optical sensors) and/or blood pressure sensor. Using this information may enable the adjustment of motion scaling factors as the user's heart rate and/or blood pressure changes. The processor may be programmed to determine, based on additional considerations or input from other sensors, whether the change in heart rate or blood pressure data should result in an increase or decrease in the scale factor. For example, if the processor determines that an increase in heart rate has occurred, but the system measures very little increase in input handle motion and an eye tracking sensor 21 determines that the user's gaze is still focused on the same portion of the image displayed on the image display, the scale factor should be low. If the heart rate increases, the user gaze location changes and there is an increase in handle motion, scaling might be increased.

3. Change in Respiratory Rate

Breathing rate is another vital sign that can be monitored similarly to heart rate. A respiratory rate sensor may be a body-worn sensor that detects deflections of the chest, such as strain gauge wearable on the user's chest or abdomen. When used in harmony with other measurements, such as those described here, breathing rate could help to increase the fidelity of the dynamic scaling control system.

4. Tone/Volume of Voice or Frequency of Verbal Communication

In this aspect, the sensor 34 may be an auditory sensor. Typically, during critical parts of procedures, the OR gets noticeably quieter. This change in detected volume could indicate a high focus moment, causing the processor to respond by applying a lower scale factor. As another example, the sensor output could be analyzed for changes in the tone of the surgeon's voice, since such changes could indicate changes in his/her level of frustration or stress. Combining this information with other data from the control system could be very useful for automatic adjustment of the scale factor.

5. Sweating/Galvanic Skin Response

In this embodiment, the sensor measures the electrical resistance of the surgeon's skin. Detected changes in the electrical resistance can be used by the processor to alter the scaling rate, as these changes may be indicators of the user's stress level. When used in conjunction with other measurements, skin response could increase the fidelity of the dynamic scaling control system.

The described surgeon monitoring sensors may additionally be used as input to a machine learning algorithm used in a surgical system in order to implement and optimize adjustments to motion scaling based on sensed user parameters such as those described herein. The sensors would be used in the robot assisted surgical system to monitor the parameters indicative of the surgeon's stress and focus level. Data would also be collected correlating those parameters with the motion of the instruments (as sensed, for example, using sensors measuring movements of the user input device and/or sensors measuring movements of the surgical instruments), the procedure being performed (as recognized by the system or input by a user), motion of the input handles, motion scaling settings selected, etc. An analysis of this procedure data with data on the sensed user parameters is thus used to build and optimize a highly effective control system for motion scaling based on an analytical model with surgeon physiological behaviors as a part of the input.

The disclosed concepts provide advantages over existing technology. Current robotic systems use menus to select the desired motion scaling. During critical moments, this can be frustrating to the user because they are unable to effectively complete the desired task without switching the motion scaling level which takes too much time. The described system causes smooth and effective motion scaling adjustment automatically such that the user would ideally not even notice a change.

All prior applications and patents referred to herein, including for purposes of priority, are incorporated herein by reference.

We claim:

1. A robot-assisted surgical system comprising:
   a robotic manipulator configured for robotic positioning of a surgical instrument in a body cavity,
   at least one user input device moveable by a user,
   at least one processor and at least one memory, the at least one memory storing instructions executable by said at least one processor to:
   receive user input in response to movement of the input device by a user,
   receive instrument type input in response to positioning of a surgical instrument on or in proximity to the manipulator,
   receive input from a user specifying a surgical procedure type,
   apply a scaling factor based on the instrument type input and the specified surgical procedure type,
   cause the manipulator to move the first surgical instrument in response to the user input, based on the scaling factor.

2. The system of claim 1, wherein, the instructions are further executable by the at least one processor to:
   predict a subsequent task to be performed based on the specified procedure type;
   receive instrument type input based on signals from the sensor in response to positioning of a second surgical instrument on, or in proximity to the robotic manipulator, and applying a scaling factor based on the instrument type input, the predicted subsequent task, and the specified procedure type.

3. The system of claim 1, wherein:
   the instructions are further executable by the at least one processor to receive input identifying a user; and the scaling factor is applied based on the instrument type input and the user identity.

4. The system of claim 1, wherein the manipulator includes at least one RFID reader, and wherein the instructions are executable by said at least one processor to receive the instrument type input based on input from the RFID reader in response to positioning of a surgical instrument on or in proximity to the RFID reader, the surgical instrument having an RFID tag.

5. The system of claim 1, wherein the system includes an optical sensor, and wherein the instructions are executable by said at least one processor to receive the instrument type input based on input from the optical sensor.

6. A robot-assisted surgical system comprising:
   a robotic manipulator configured for robotic positioning of a surgical instrument in a body cavity,
   at least one user input device moveable by a user,
   at least one processor and at least one memory, the at least one memory storing instructions executable by said at least one processor to:
   receive user input in response to movement of the input device by a user,
   receive instrument type input in response to positioning of a surgical instrument on or in proximity to the manipulator,
   receive input identifying a user,
   apply a scaling factor based on the instrument type input and the identified user,
   cause the manipulator to move the first surgical instrument in response to the user input, based on the scaling factor.

7. The system of claim 6, wherein the system includes at least one biometric sensor, and wherein the instructions are executable by said at least one processor to receive input identifying a user based on input from the at least one biometric sensor.

8. The system of claim 7, wherein the at least one biometric sensor is at least one of an image sensor configured for facial recognition, an eye scanner, a fingerprint scanner, or a voice sensor.

9. The sensor of claim 6, wherein the system includes an auxiliary input device comprising at least one of a graphical user interface, touch screen, keyboard or mouse, and wherein the instructions are executable by said at least one processor to receive input identifying a user based on input from said auxiliary input device.

10. The system of claim 6, wherein the system includes a user identification sensor configured to scan a user identification device, wherein the instructions are executable by said at least one processor to receive input identifying a user based on input from said user identification device.

11. The system of claim 6, wherein the user identification device comprises at least one of an identification wristband or badge.

* * * * *